US009744310B2

(12) United States Patent
Kondoh et al.

(10) Patent No.: US 9,744,310 B2
(45) Date of Patent: Aug. 29, 2017

(54) PHARMACEUTICAL INJECTION DEVICE

(75) Inventors: Tsuguhiro Kondoh, Ehime (JP); Seiji Kikuchi, Ehime (JP); Takashi Hanada, Hyogo (JP)

(73) Assignees: PANASONIC HEALTHCARE CO., LTD., Ehime (JP); JCR PHARMACEUTICALS CO., LTD., Hyogo (JP)

( * ) Notice: Subject to any disclaimer, the term of this patent is extended or adjusted under 35 U.S.C. 154(b) by 470 days.

(21) Appl. No.: 14/343,504

(22) PCT Filed: Sep. 10, 2012

(86) PCT No.: PCT/JP2012/005712
§ 371 (c)(1),
(2), (4) Date: Mar. 7, 2014

(87) PCT Pub. No.: WO2013/038640
PCT Pub. Date: Mar. 21, 2013

(65) Prior Publication Data
US 2014/0221925 A1    Aug. 7, 2014

(30) Foreign Application Priority Data
Sep. 12, 2011   (JP) ................................ 2011-198099

(51) Int. Cl.
*A61M 5/315*    (2006.01)
*A61M 5/20*     (2006.01)
(Continued)

(52) U.S. Cl.
CPC .......... *A61M 5/31568* (2013.01); *A61M 5/20* (2013.01); *A61M 5/31576* (2013.01);
(Continued)

(58) Field of Classification Search
CPC .......... A61M 5/31568; A61M 5/31576; A61M 5/20; A61M 2005/3125; A61M 5/2066;
(Continued)

(56) References Cited

U.S. PATENT DOCUMENTS 5,322,511 A    6/1994  Armbruster et al.
6,159,161 A   12/2000  Hodosh
(Continued)

FOREIGN PATENT DOCUMENTS

JP    H11513586 A    11/1999
JP    2006-034719 A   2/2006
(Continued)

OTHER PUBLICATIONS

Office action for Application No. JP 2013-533487 dated Jun. 2, 2015.
(Continued)

*Primary Examiner* — Kevin C Sirmons
*Assistant Examiner* — Amber Stiles
(74) *Attorney, Agent, or Firm* — Pearne & Gordon LLP

(57) ABSTRACT

The pharmaceutical injection device includes a pharmaceutical syringe mounting portion (3) provided within a main body case (2) and to which a pharmaceutical syringe (4) is removably mounted, a piston (5) provided movably with respect to the pharmaceutical syringe (4) mounted to the pharmaceutical syringe mounting portion (3), a drive mechanism (6) for driving the piston (5), a controller (7) that is electrically connected to the drive mechanism (6), a display section (35) that is connected to the controller (7), and an encoder (26) that is connected to the controller (7) and detects the amount of the pharmaceutical remaining inside the pharmaceutical syringe (4). The controller (7) displays a warning on the display section (35) recommending removal of the pharmaceutical syringe (4) from the
(Continued)

pharmaceutical syringe mounting portion (3) when the presence of a pharmaceutical is detected by the encoder (26).

2 Claims, 11 Drawing Sheets

(51) Int. Cl.
  *A61M 5/32* (2006.01)
  *A61M 5/145* (2006.01)
  *A61M 5/168* (2006.01)
  *A61M 5/31* (2006.01)

(52) U.S. Cl.
  CPC ....... *A61M 5/14566* (2013.01); *A61M 5/1684* (2013.01); *A61M 5/2066* (2013.01); *A61M 5/31546* (2013.01); *A61M 5/31593* (2013.01); *A61M 5/326* (2013.01); *A61M 2005/14573* (2013.01); *A61M 2005/206* (2013.01); *A61M 2005/3125* (2013.01); *A61M 2005/31588* (2013.01); *A61M 2205/14* (2013.01); *A61M 2205/215* (2013.01); *A61M 2205/3606* (2013.01); *A61M 2205/50* (2013.01)

(58) Field of Classification Search
  CPC .......... A61M 5/14566; A61M 5/31546; A61M 5/31593; A61M 5/1684; A61M 5/326; A61M 2005/14573; A61M 2005/31588; A61M 2005/206; A61M 2205/3606; A61M 2205/14; A61M 2205/215; A61M 2205/50
  See application file for complete search history.

(56) References Cited

U.S. PATENT DOCUMENTS

| | | | |
|---|---|---|---|
| 6,544,200 | B1 | 4/2003 | Smith et al. |
| 7,749,186 | B2 | 7/2010 | Kohlbrenner et al. |
| 8,211,067 | B2 | 7/2012 | Nemoto |
| 8,398,602 | B2 | 3/2013 | Iio et al. |
| 8,556,847 | B2 | 10/2013 | Kohlbrenner et al. |
| 8,771,233 | B2 | 7/2014 | Watanabe et al. |
| 2004/0210199 | A1* | 10/2004 | Atterbury ......... A61M 5/31566 604/224 |
| 2005/0171476 | A1 | 8/2005 | Judson |
| 2005/0197650 | A1* | 9/2005 | Sugimoto ............... A61M 5/20 604/890.1 |
| 2006/0151049 | A1 | 7/2006 | Nemoto |
| 2007/0021715 | A1 | 1/2007 | Kohlbrenner |
| 2007/0142777 | A1* | 6/2007 | Klein ..................... G01N 21/11 604/152 |
| 2009/0131756 | A1 | 5/2009 | Nemoto |
| 2009/0299328 | A1 | 12/2009 | Mudd et al. |
| 2010/0238038 | A1 | 9/2010 | Kohlbrenner et al. |
| 2010/0262078 | A1* | 10/2010 | Blomquist ........ A61M 5/14244 604/151 |
| 2011/0144574 | A1 | 6/2011 | Kamen et al. |
| 2011/0218502 | A1 | 9/2011 | Iio et al. |
| 2011/0238017 | A1 | 9/2011 | Watanabe et al. |
| 2011/0257602 | A1 | 10/2011 | Watanabe et al. |
| 2011/0313349 | A1 | 12/2011 | Krulevitch et al. |
| 2011/0313350 | A1 | 12/2011 | Krulevitch et al. |
| 2011/0313395 | A1 | 12/2011 | Krulevitch et al. |
| 2012/0004637 | A1 | 1/2012 | Krulevitch et al. |
| 2012/0323176 | A1 | 12/2012 | Watanabe et al. |
| 2013/0175192 | A1 | 7/2013 | Iio et al. |

FOREIGN PATENT DOCUMENTS

| | | |
|---|---|---|
| WO | 97/14459 A1 | 4/1997 |
| WO | 2006/059597 A1 | 6/2006 |
| WO | 2010/055608 A1 | 5/2010 |
| WO | 2010070799 A1 | 6/2010 |
| WO | 2010/073452 A1 | 7/2010 |
| WO | 2010/098931 A1 | 9/2010 |
| WO | 2011/108225 A1 | 9/2011 |

OTHER PUBLICATIONS

Extended European Search Report for Application No. 12831697.3 dated Dec. 5, 2014.
International Search Report for PCT/JP2012/005712 dated Oct. 23, 2012.
U.S. Non-Final Rejection for U.S. Appl. No. 14/343,548 dated Jun. 15, 2016.
Final Office Action issued in U.S. Appl. No. 14/343,548 dated Dec. 2, 2016.
Notice of Allowance and Fee(s) Due issued in U.S. Appl. No. 14/343,548 dated Feb. 10, 2017.

* cited by examiner

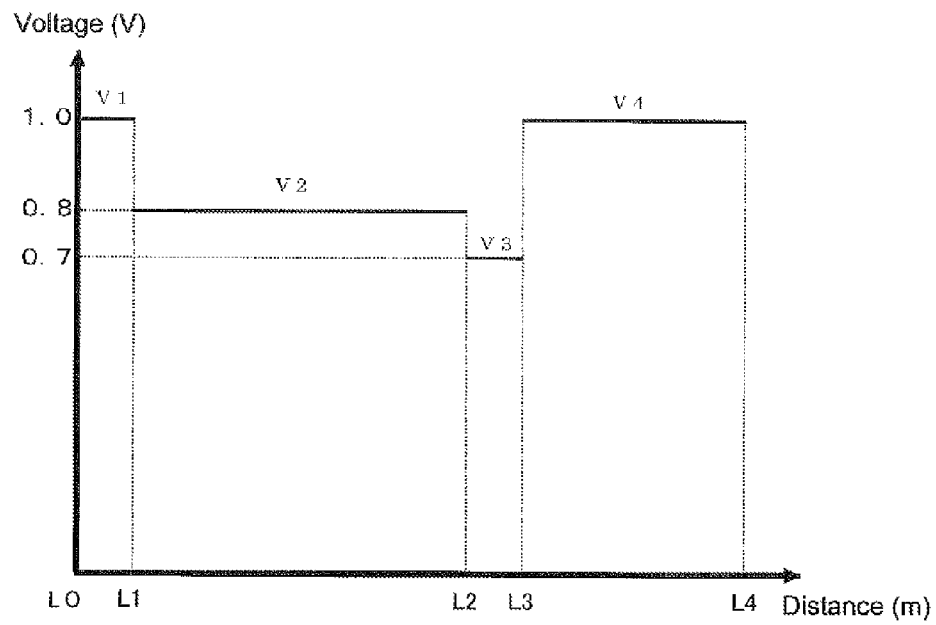

L0: initial position of separation gasket rear end
L1: position when separation gasket rear end touches bypass
 (at start of mixing operation)
L2: position when separation gasket rear end touches push-in gasket
 (at end of mixing operation)
L3: position of separation gasket rear end after completion of air venting operation
L4: position of separation gasket rear end after completion of pharmaceutical injection operation

FIG. 8

L1 (before mixing operation)
L0 (initial position)

L2 (at completion of mixing operation)
L1 (before mixing operation)
L0 (initial position)

PHARMACEUTICAL INJECTION DEVICE

TECHNICAL FIELD

The present invention relates to a pharmaceutical injection device.

BACKGROUND ART

A conventional pharmaceutical injection device comprises a main body case having an injection needle insertion and retraction opening, a pharmaceutical syringe mounting portion provided inside this main body case, a pharmaceutical syringe mounted to this pharmaceutical syringe mounting portion, a piston provided movably with respect to this pharmaceutical syringe, a drive mechanism that drives this piston, and a controller that is electrically connected to this drive mechanism.

The pharmaceutical syringe has a cylinder and a push-in gasket provided on the rear end side inside this cylinder.

That is, with a conventional pharmaceutical injection device, the pharmaceutical is injected into the body by pushing the push-in gasket with the piston (see Patent Literature 1, for example).

CITATION LIST

Patent Literature

Patent Literature 1: Japanese Unexamined Patent Application Publication (Translation of PCT Application) No. H11-513586

SUMMARY

Technical Problem

However, the following problem was encountered with the conventional pharmaceutical injection device discussed above.

Specifically, with the pharmaceutical injection device disclosed in the above-mentioned publication, properly managing the pharmaceutical syringe was difficult.

With a pharmaceutical syringe that contains number of doses of pharmaceutical, once a single pharmaceutical injection is over, this pharmaceutical syringe is removed from the pharmaceutical syringe mounting portion and stored in a refrigerator, for example. However, if the user forgets to remove a pharmaceutical syringe that still contains some pharmaceutical, then the management of that pharmaceutical syringe cannot be carried out properly.

It is an object of the present invention to provide a pharmaceutical injection device with which the management of a pharmaceutical syringe can be carried out properly.

Solution to Problem

To achieve the stated object, the pharmaceutical injection device of the present invention comprises a main body case, a pharmaceutical syringe mounting portion, a piston, a drive mechanism, a controller, a display section, and a remaining pharmaceutical sensor. The main body case has an opening through which an injection needle is inserted and retracted. The pharmaceutical syringe mounting portion is provided inside the main body case, and a pharmaceutical syringe is removably mounted thereto. The piston is provided movably with respect to the pharmaceutical syringe mounted to the pharmaceutical syringe mounting portion. The drive mechanism drives the piston. The controller is electrically connected to the drive mechanism. The display section is connected to the controller. The remaining pharmaceutical sensor is connected to the controller and senses the amount of pharmaceutical remaining in the pharmaceutical syringe. If the presence of a pharmaceutical is detected by the remaining pharmaceutical sensor, the controller causes the display section to display a warning recommending removal of the pharmaceutical syringe from the pharmaceutical syringe mounting portion.

Advantageous Effects

With the pharmaceutical injection device pertaining to the present invention, a warning is displayed on the display section, so if there is any pharmaceutical remaining in the pharmaceutical syringe, the user can be prompted to remove the pharmaceutical syringe from the pharmaceutical syringe mounting portion and store it in a refrigerator or the like, and as a result, management of the pharmaceutical syringe can be carried out properly.

BRIEF DESCRIPTION OF DRAWINGS

FIG. 8 is a graph of the operating state during mixing in the pharmaceutical injection device in FIG. 1;

DESCRIPTION OF EMBODIMENTS

The pharmaceutical injection device pertaining to an embodiment of the present invention will now be described through reference to the appended drawings.

Embodiment 1

Figure 1:
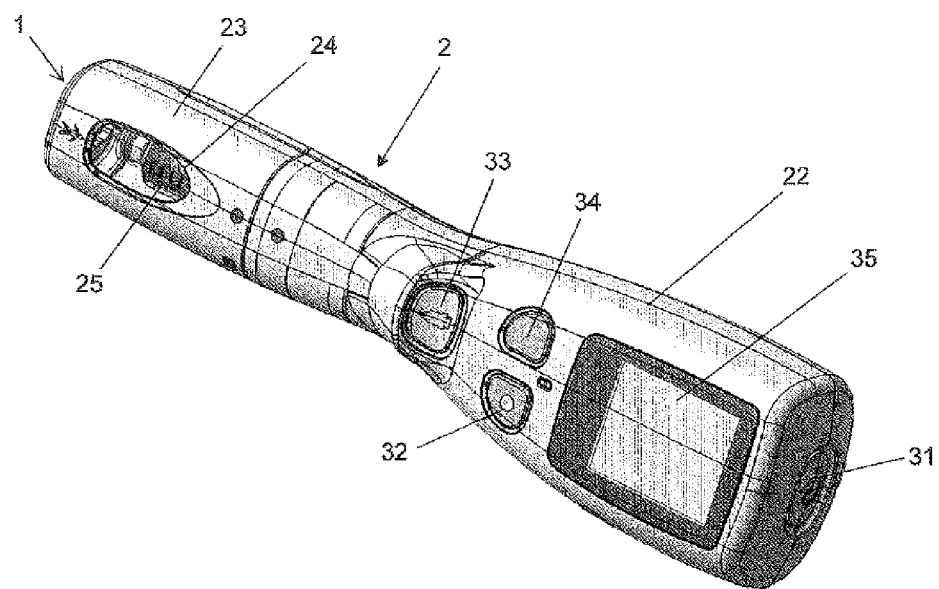
FIG. 1 is an oblique view of the pharmaceutical injection device pertaining to an embodiment of the present invention.
Figure 2:
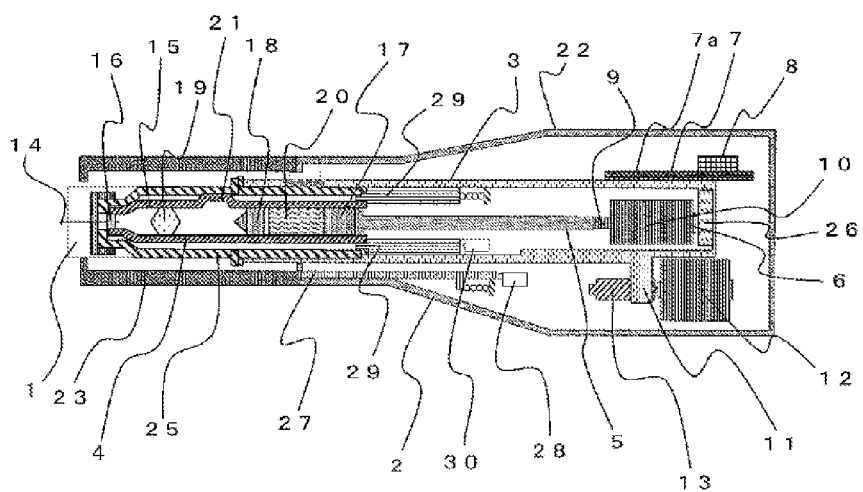
FIG. 2 is a cross section of the pharmaceutical injection device in FIG. 1.

As shown in FIGS. 1 and 2, the pharmaceutical injection device in this embodiment comprises a substantially cylindrical main body case 2, a pharmaceutical syringe mounting portion 3, a pharmaceutical syringe 4, a piston 5, a drive mechanism 6, a controller 7, and an orientation sensor 8. The main body case 2 has an injection needle insertion and retraction opening 1 on its distal end side. The pharmaceutical syringe mounting portion 3 is provided inside the main body case 2. The pharmaceutical syringe 4 is mounted inside the pharmaceutical syringe mounting portion 3. The piston 5 is provided movably with respect to the pharmaceutical syringe 4. The drive mechanism 6 drives the piston 5. The controller 7 is electrically connected to the drive mechanism 6. The orientation sensor 8 is electrically connected to the controller 7.

The orientation sensor 8 is mounted on a substrate 7a having the controller 7. The substrate 7a is installed so as to be parallel to the drive direction of the piston 5.

The drive mechanism 6 is made up of a bolt 9 inserted into a rear end opening in the piston 5, and a piston drive motor 10 for driving the bolt 9. Specifically, when the piston drive motor 10 is rotated in one direction, the bolt 9 pushes the piston 5 toward the injection needle insertion and retraction opening 1. Conversely, when the piston drive motor 10 is rotated in the other direction, the piston 5 is pulled back toward the piston drive motor 10.

The piston drive motor 10 and the piston 5 are disposed along with the pharmaceutical syringe 4 inside the pharmaceutical syringe mounting portion 3. Female threads 11 are provided toward the outside of the rear end side of the pharmaceutical syringe mounting portion 3. A bolt 13 of a needle insertion and retraction drive motor 12 meshes with these female threads 11. That is, when the needle insertion and retraction drive motor 12 is driven, the female threads 11 and the bolt 13 mesh, causing the pharmaceutical syringe mounting portion 3 to move back and forth with respect to the injection needle insertion and retraction opening 1. This causes an injection needle 14 provided on the distal end side of the pharmaceutical syringe 4 to come out of the injection needle insertion and retraction opening 1.

Figure 9A:
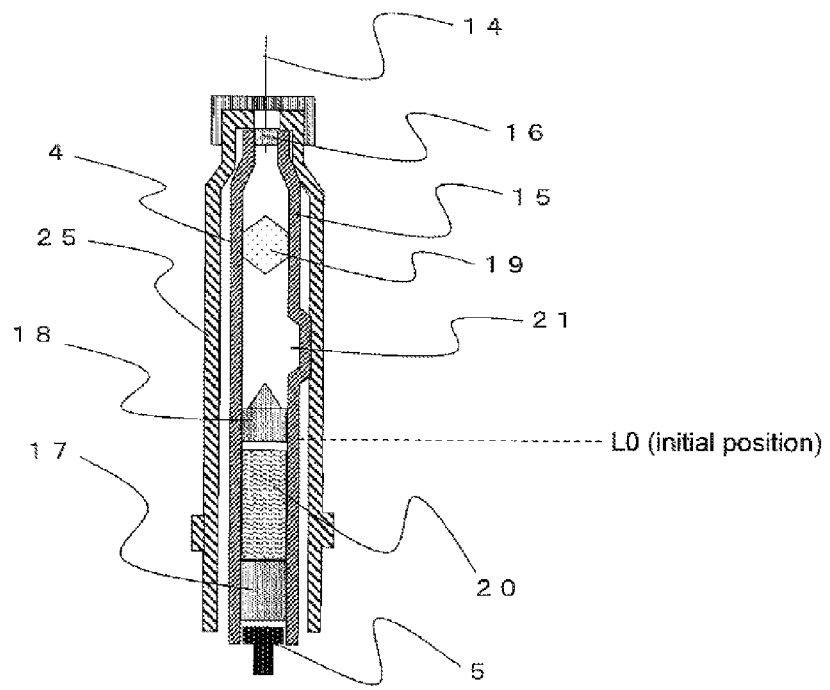
FIG. 9A is a cross section of the operating state during mixing in the pharmaceutical injection device in FIG. 1.

As shown in FIG. 9A, the pharmaceutical syringe 4 has a cylinder 15, a distal end gasket 16, a push-in gasket 17, a separation gasket 18, a solid pharmaceutical 19, a liquid pharmaceutical 20, and a bypass 21. The distal end gasket 16 is provided on the distal end side inside the cylinder 15. The push-in gasket 17 is provided on the rear end side inside the cylinder 15. The separation gasket 18 is provided in the middle inside the cylinder 15. The solid pharmaceutical 19 is contained inside the cylinder 15 between the distal end gasket 16 and the separation gasket 18. The liquid pharmaceutical 20 is contained inside the cylinder 15 between the push-in gasket 17 and the separation gasket 18. The bypass 21 protrudes in the outer peripheral direction of the cylinder 15 at the portion of the cylinder 15 between the distal end gasket 16 and the separation gasket 18.

The controller 7 actuates the drive mechanism 6 so that the push-in gasket 17 is pressed by the piston 5 to the distal end gasket 16 side after orientation and position sensing by the orientation sensor 8.

Also, the rate at which the push-in gasket 17 is pushed in by the piston 5 is set so that if we let V1 be the push-in rate when the separation gasket 18 reaches the bypass 21, V2 be the push-in rate at the point when the separation gasket 18 goes through the bypass 21, V3 be the push-in rate at the point when air is vented after the separation gasket 18 has gone through the bypass 21, and V4 be the push-in rate at the point when a pharmaceutical is injected after air venting, the push-in rate V2 will be lower than the push-in rate V1.

Returning to FIGS. 1 and 2, the main body case 2 is made up of a housing 22 and a distal end cap 23 on the distal end side of the housing 22. The distal end cap 23 is removably mounted to the housing 22. A window 24 is provided on the outer peripheral part of the distal end cap 23.

After the pharmaceutical syringe 4 has been mounted inside the pharmaceutical syringe mounting portion 3, the outer periphery of the pharmaceutical syringe 4 is covered by a syringe cover 25 (see FIG. 9A, etc.). In this state, the injection needle 14 is mounted to the distal end gasket 16 on the distal end side of the pharmaceutical syringe 4.

When the piston 5 pushes the push-in gasket 17 forward, the liquid pharmaceutical 20 goes through the bypass 21 and flows to the solid pharmaceutical 19 side, and when the push-in gasket 17 moves farther forward, the mixture of solid pharmaceutical 19 and liquid pharmaceutical 20 flows out of the injection needle 14.

The rotation of the piston drive motor 10 is detected by an encoder 26. Consequently, the amount by which the piston 5 protrudes (moves) is sensed. The solid pharmaceutical 19 and the liquid pharmaceutical 20 contained inside the pharmaceutical syringe 4 are put in at a pharmaceutical company, etc.

The housing 22 of the main body case 2 also houses a number of switches. More specifically, a distal end cap detector switch 28 is disposed at the rear end of a control rod 27 provided around the outer periphery of the pharmaceutical syringe mounting portion 3, on the distal end side of the housing 22. When the distal end cap 23 is mounted to the distal end of the housing 22, the control rod 27 is pushed rearward, and the distal end cap detector switch 28 detects that the distal end cap 23 has been mounted.

A control rod 29 is disposed inside the pharmaceutical syringe mounting portion 3. When the control rod 29 is pushed rearward by the syringe cover 25, a syringe cover detector switch 30 detects that the syringe cover 25 has been mounted.

The orientation sensor 8 is mounted on the substrate 7a having the controller 7. Since the substrate 7a is installed so as to be parallel to the drive direction of the piston 5, the orientation sensor 8 can properly sense acceleration with respect to the main body case 2. In this embodiment, the substrate 7a is installed parallel to the drive direction of the piston 5, but may instead be installed perpendicular to the drive direction of the piston 5.

Returning to FIG. 1, various control buttons and so forth are provided to the outer periphery of the housing 22 of the main body case 2. More specifically, a power button 31 is provided to the rear end of the housing 22. A mix button 32, a pharmaceutical injection button 33, an end button 34, and a display section 35 are provided to the outer periphery of the housing 22.

Figure 3:
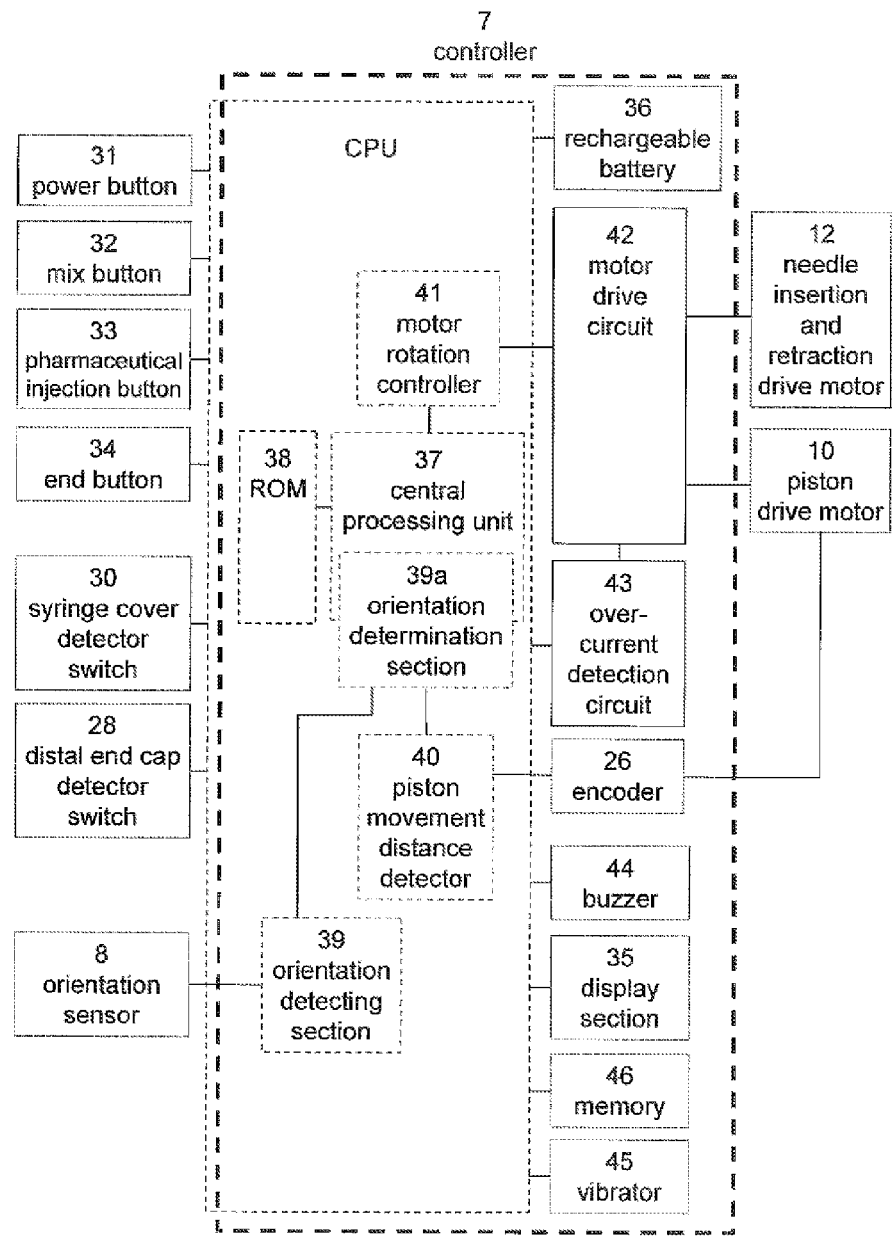
FIG. 3 is a control block diagram of the simplified electrical configuration of the pharmaceutical injection device in FIG. 1.

FIG. 3 is an electrical block diagram of the pharmaceutical injection device in FIG. 1.

The controller 7 is constituted by a microprocessor. As shown in FIG. 3, a rechargeable battery 36 is connected to the controller 7 and other electrically driven parts. The electrical connection state of the rechargeable battery 36 and the other electrically driven parts is not shown, to keep FIG. 3 from being too complicated.

A central processing unit 37 is provided inside the controller 7. The central processing unit 37 performs operational control over the various blocks shown in FIG. 3. A program that performs this operational control is written into a ROM 38. An orientation detecting section 39, a piston movement distance sensor 40, and a motor rotation controller 41 are connected to the central processing unit 37.

An orientation determination section 39a and the orientation sensor 8 are connected to the orientation detecting section 39. The orientation detecting section 39 converts the orientation sensing result from the orientation sensor 8 into information for determining the orientation at the orientation determination section 39a.

The orientation determination section 39a performs various kinds of operational control according to the orientation, such as using the orientation information obtained from the orientation detecting section 39 to compare the inclination sensed by the orientation sensor 8 with a set value, determine whether or not to drive the piston drive motor 10, etc.

The piston movement distance detector 40 is connected to the encoder 26. The encoder 26 is attached to the piston drive motor 10, which allows the movement distance of the piston 5 to be detected by detecting the rotation of the piston drive motor 10.

The motor rotation controller 41 is connected to a motor drive circuit 42. When the value detected by the piston movement distance detector 40 reaches a preset value, the motor rotation controller 41 controls the motor drive circuit 42 to change the movement speed of the piston 5.

The piston drive motor 10 and the needle insertion and retraction drive motor 12 are connected to the motor drive circuit 42. The motor drive circuit 42 is connected to an over-current detection circuit 43.

The motor drive circuit 42 is controlled by the motor rotation controller 41, and drives the piston drive motor 10 and the needle insertion and retraction drive motor 12.

The over-current detection circuit 43 is a circuit that detects the amount of current from the motor drive circuit 42, and detects malfunction in the motors.

The controller 7 is also connected to a buzzer 44 and a vibrator 45 for issuing a warning so as to alert the user to the status of the device.

The controller 7 is also connected to the display section 35, which displays warnings and information for operating the device, and to a memory 46 for recording various kinds of data.

The above configuration will now be described through reference to the operational flowchart shown in FIG. 4.

Figure 4:
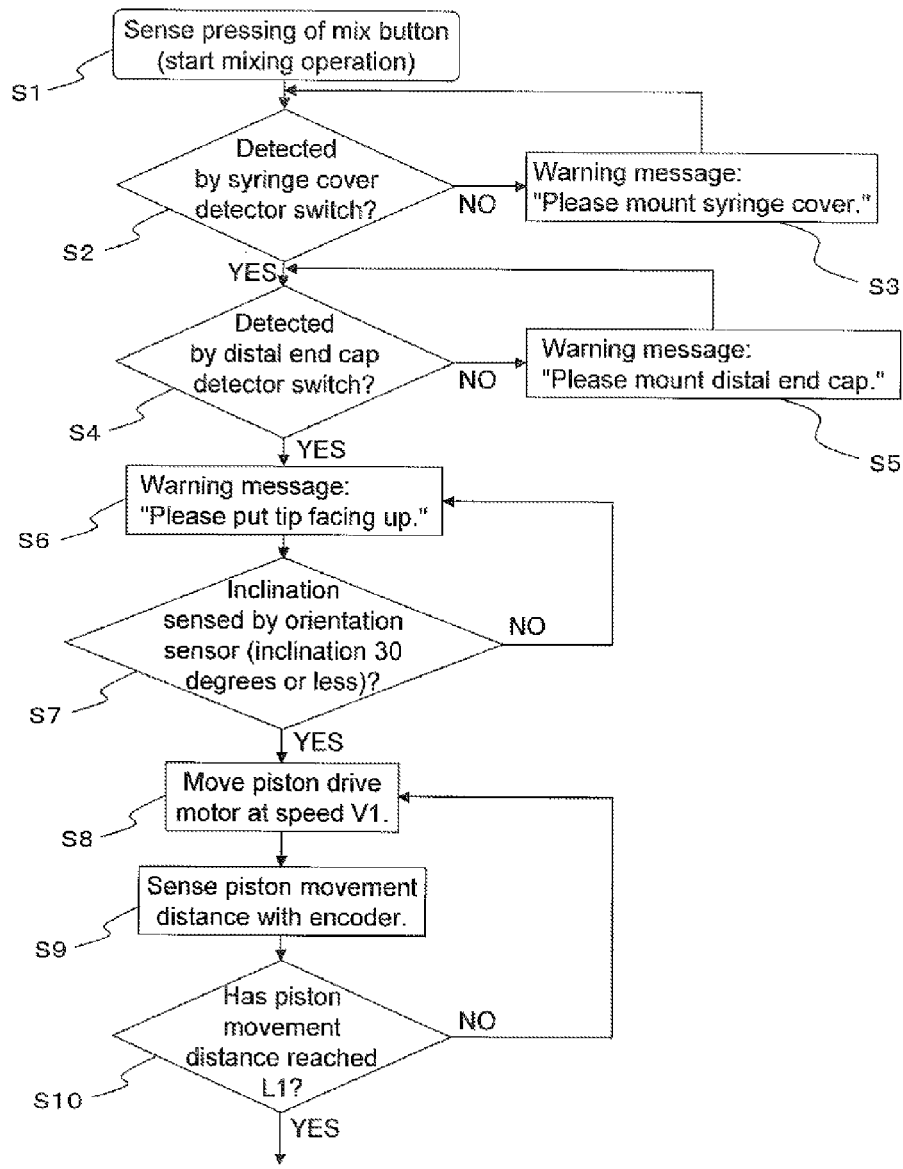
FIG. 4 is a flowchart of the operational control of the pharmaceutical injection device in FIG. 1.

First, as shown in FIG. 4, the mix button 32 (see FIG. 1) is pressed in S1.

Then, in S2, the syringe cover detector switch 30 detects whether or not the syringe cover 25 has been mounted. If the syringe cover 25 has not been mounted, as shown in S3, a warning display of "Please mount syringe cover" is given on the display section 35 (see FIG. 1).

Once the mounting of the syringe cover 25 has been confirmed, the distal end cap detector switch 28 checks whether or not the distal end cap 23 has been mounted, as shown in S4. Here again, as shown in S5, if the distal end cap 23 has not been mounted, a warning display of "Please mount distal end cap" is given on the display section 35.

The following operation is not performed if the syringe cover 25 and the distal end cap 23 have not been mounted, as shown in S2 and S4.

In S2 and S4, once it has been confirmed that the syringe cover 25 and the distal end cap 23 have been mounted, a display of "Please put tip facing up" is left on the display section 35 for a specific length of time.

In S7, the inclination of the pharmaceutical injection device is sensed by the orientation sensor 8. Hereinafter, the inclination will be referred to by using the direction perpendicular to the horizontal plane as zero degrees. If the inclination exceeds a specific value (the set value), the operation is halted until the inclination falls back to within the specific value (the set value), and operation is restarted once the inclination has been within the specific value for a specific length of time. When leakage from the injection needle is taken into account, it is preferable for the inclination at which operation is performed to be 30 degrees or less.

Figure 7:
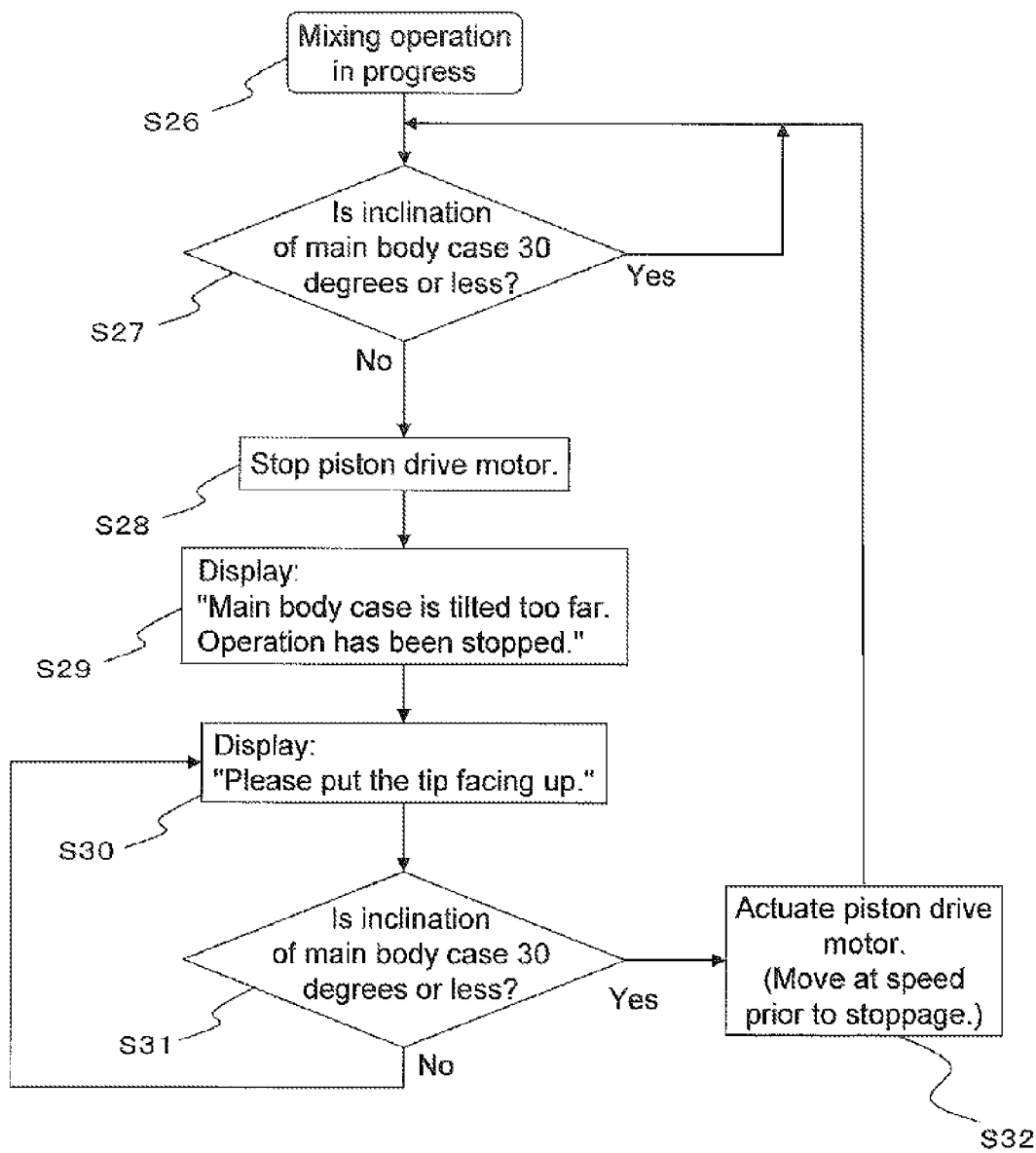
FIG. 7 is a flowchart of the operational control of the pharmaceutical injection device in FIG. 1.

Although not discussed in detail here, the inclination is continuously sensed by the orientation sensor 8 during the operation from S7 onward, as shown in FIG. 7 (S26). Here, if the inclination of the main body case 2 exceeds 30 degrees (S27), the piston drive motor 10 is stopped (S28), and the display section 35 gives a warning display of "Main body case is tilted too far. Operation has been stopped" (S29) and "Please put the tip facing up" (S30). This prompts the user not to tilt the main body case 2 more than 30 degrees. S31 is a loop with S30, and is used to check whether the inclination of the main body case 2 has exceeded 30 degrees.

S32 is used to restart the operation prior to the stoppage, and return to S8 in the event that it is sensed in S31 that the inclination is 30 degrees or less.

Figure 9B:
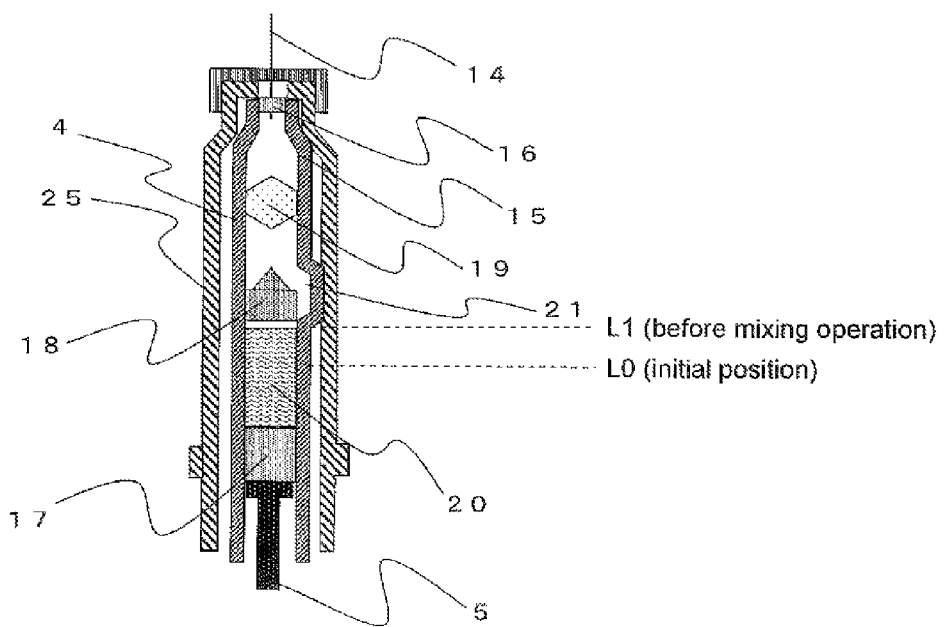
FIG. 9B is a cross section of the operating state during mixing in the pharmaceutical injection device in FIG. 1.

In S8, as shown in FIG. 9A, the piston drive motor 10 is driven from its initial state prior to the mixing operation, at the push-in rate V1. Then, in S9, the movement distance of the piston 5 is calculated by the encoder 26 during drive of the piston 5. Then, in S10, the piston drive motor 10 continues to move at the push-in rate V1 until the rear end of the separation gasket 18 goes from L0 in FIG. 9B (the initial position) to the position L1 a specific distance away. As shown in FIG. 9B, L1 indicates the position where the rear end of the separation gasket 18 touches the bypass 21, and is position information about the movement distance from the initial position L0 to L1, that is, until the rear end of the separation gasket 18 changes from its initial state to a contact state. This L1 position information is stored ahead of time in the memory 46.

Figure 5:
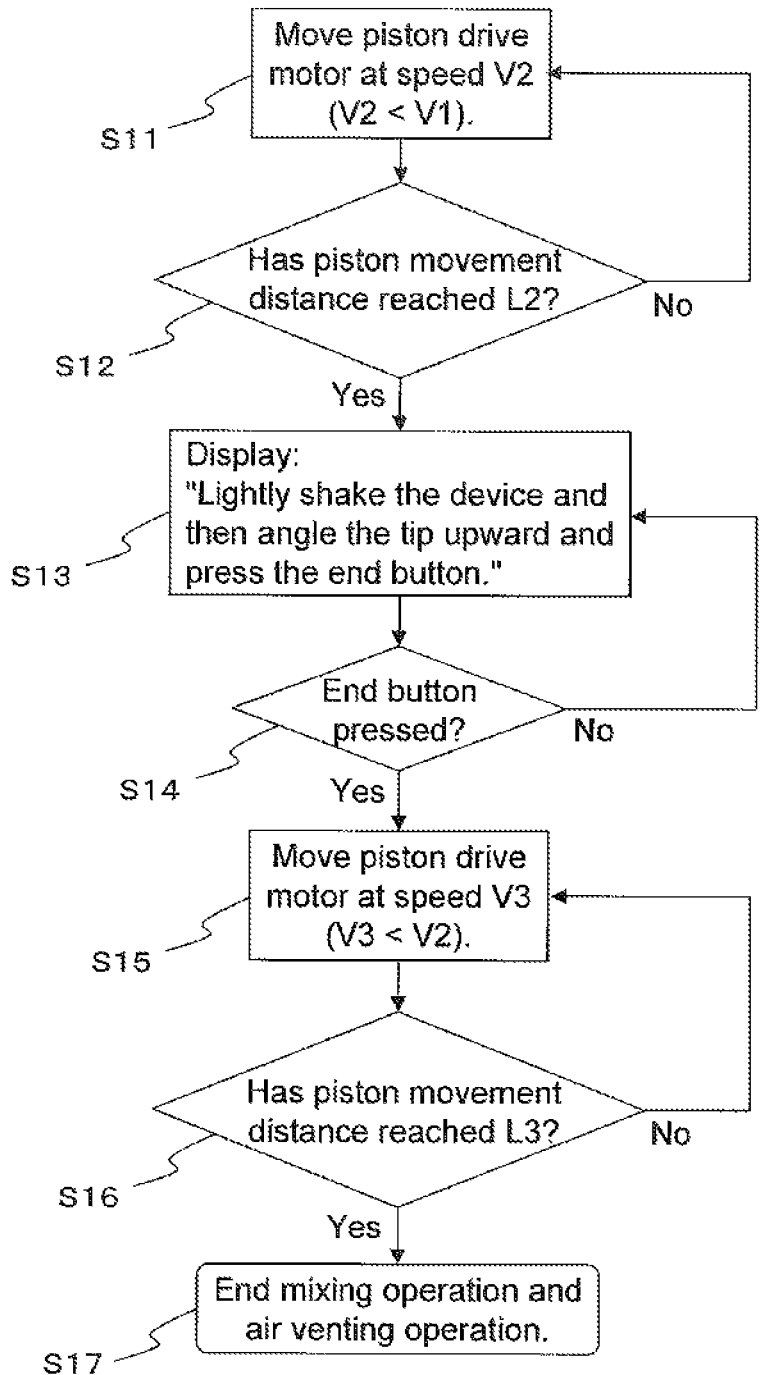
FIG. 5 is a flowchart of the operational control of the pharmaceutical injection device in FIG. 1.

When the rear end of the separation gasket 18 reaches the position L1, the mixing operation commences. As shown in S11 in FIG. 5, the push-in rate V2 of the separation gasket by the piston drive motor 10 is switched so as to be lower than the push-in rate V1 (V2<V1).

Figure 9C:
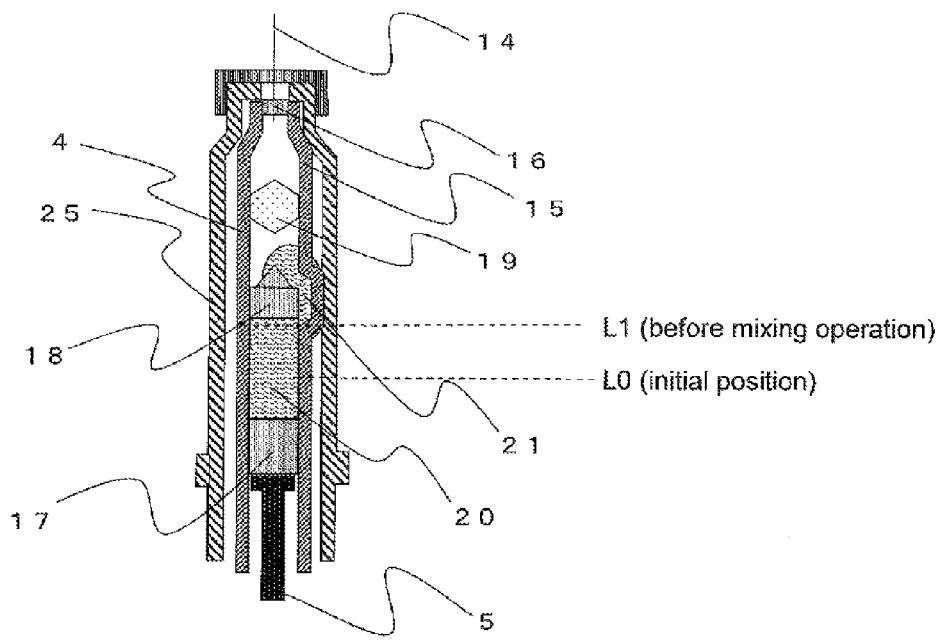
FIG. 9C is a cross section of the operating state during mixing in the pharmaceutical injection device in FIG. 1.

As shown in FIG. 9C, when the rear end of the separation gasket 18 starts to pass through the bypass 21, the liquid pharmaceutical 20 begins to flow through the bypass 21 to the solid pharmaceutical 19 side.

Figure 9D:
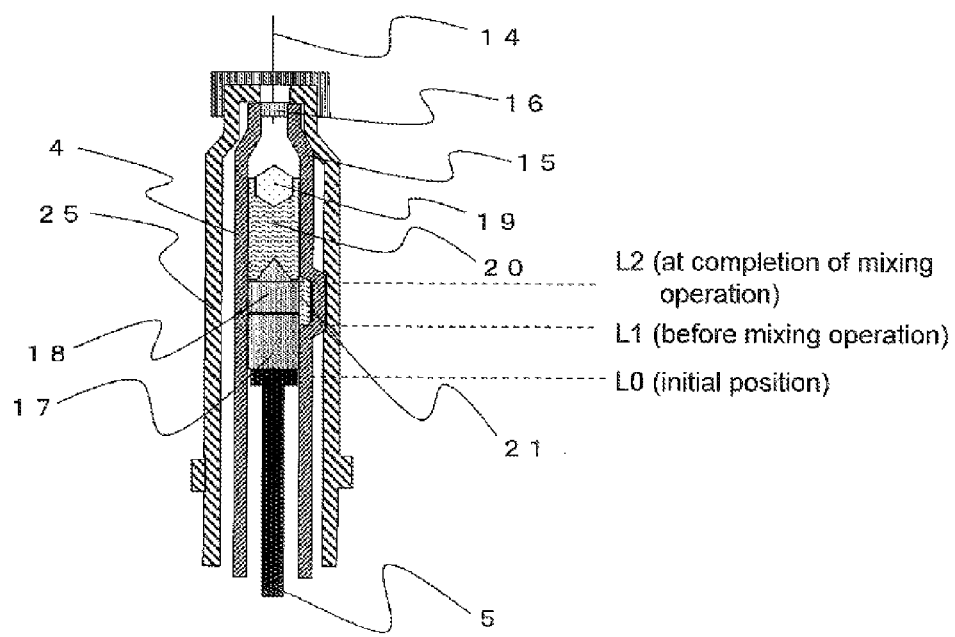
FIG. 9D is a cross section of the operating state during mixing in the pharmaceutical injection device in FIG. 1.

Then, in S12, the piston drive motor 10 continues to move at the push-in rate V2 until the distal end of the separation gasket 18 reaches the position L2 shown in FIG. 9D. The movement distance from the position L1 to the position L2, as shown in FIG. 9D, is the movement distance up until the separation gasket 18 and the push-in gasket 17 come into contact, that is, it is the movement distance until the separation gasket 18 goes from its initial state to a state of being in contact with the push-in gasket 17. This L2 position information is stored ahead of time in the memory 46.

Because the push-in rate V2 of the separation gasket 18 by the piston drive motor 10 is thus set to be lower than the push-in rate V1, it is less likely that there will be a sudden surge in pressure on the solid pharmaceutical 19 side when the liquid pharmaceutical 20 passes through the bypass 21. As a result, this prevents some of the liquid pharmaceutical from squirting out of the distal end of the injection needle 14 mounted to the distal end gasket 16 of the cylinder 15, or from overflowing more than necessary. That is, liquid leakage from the distal end of the injection needle 14 is also reduced during pharmaceutical mixing, so the mixing operation can be carried out more favorably.

Next, as shown in FIG. 9D, when the distal end position of the separation gasket 18 reaches the position L2, the display section 35 displays "Lightly shake the device and then angle the tip upward and press the end button" as shown in S13, and the operation of the piston drive motor 10 is temporarily halted. Also, the sensing of orientation is not carried out from the time of the above display until the end button 34 is pressed.

Next, in S14, air venting starts when the end button 34 is pressed (see FIG. 1).

In the air venting operation, while the inclination is being sensed by the orientation sensor 8, the push-in rate of the separation gasket 18 by the piston drive motor 10 is switched to a push-in rate V3 so as to be lower than the push-in rate V1 (V3<V1). More preferably, as in this embodiment, the push-in rate V3 is set to be lower than the push-in rate V2 (V3<V2).

In S15, since liquid is most apt to leak from the distal end of the injection needle 14 during the air venting operation, the speed at which the piston 5 is moved is further lowered.

Figure 9E:
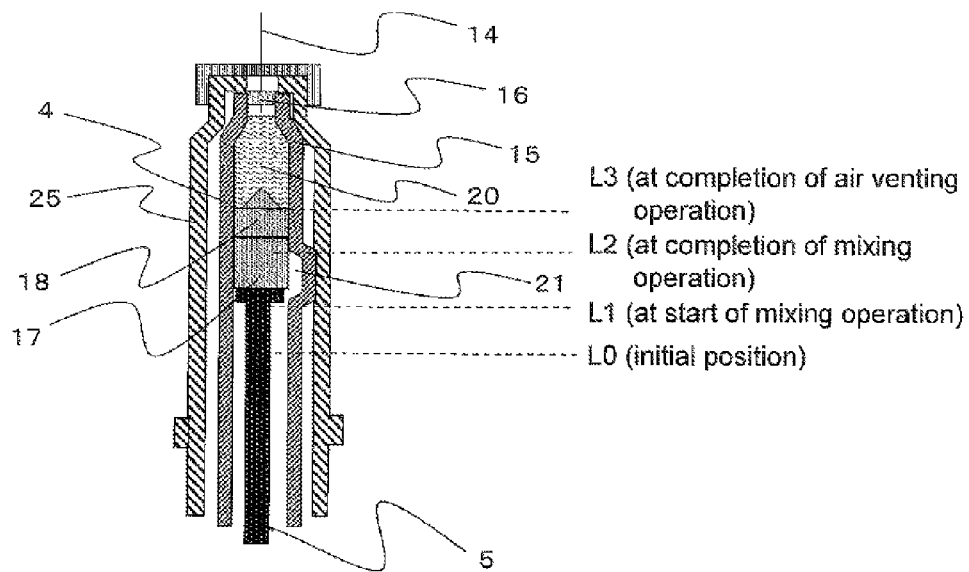
FIG. 9E is a cross section of the operating state during mixing in the pharmaceutical injection device in FIG. 1.

Then, in S16, the piston drive motor 10 is operated at the push-in rate V3 until the distal end position of the separation gasket 18 arrives at the position L3. As shown in FIG. 9E, the movement distance from the position L2 to the position L3 indicates the position after the separation gasket 18 and the push-in gasket 17 have passed through the bypass 21 in a state of being in contact with each other. Position information about the position L3 is stored ahead of time in the memory 46.

As shown in S17, the air vent operation is complete when the distal end position of the separation gasket 18 reaches the position L3.

Figure 6:
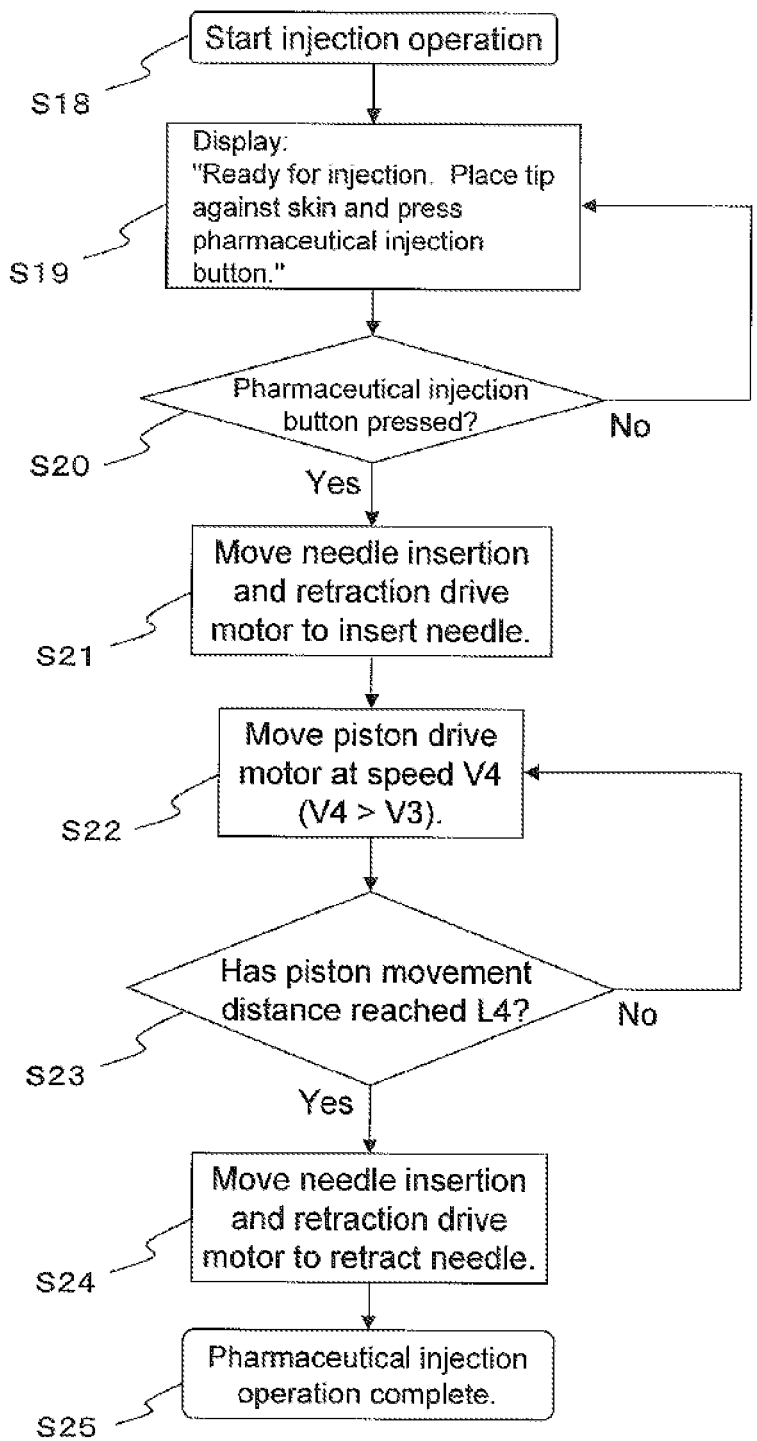
FIG. 6 is a flowchart of the operational control of the pharmaceutical injection device in FIG. 1.

The pharmaceutical injection operation shown in 818 in FIG. 6 is then commenced.

When the automatic mixing and air venting operation discussed above is complete, in S19 the display section 35 displays a message of "Ready for injection. Place tip against skin and press pharmaceutical injection button" and the operation of the piston drive motor 10 is temporarily halted.

Next, in S20, the operation of piercing the skin is commenced when the pharmaceutical injection button 33 is pressed.

Next, in S21, the needle insertion and retraction drive motor 12 is driven to perform the needle insertion operation. This "needle insertion operation" refers to an operation of driving the needle insertion and retraction drive motor 12 to move the pharmaceutical syringe mounting portion 3 to the injection needle insertion and retraction opening 1 side, and thereby causing the injection needle 14 to stick out from the injection needle insertion and retraction opening 1.

At this point, since the injection needle insertion and retraction opening 1 is already being pressed against the site on the body where the injection is to be made, the injection needle 14 is moved toward the body and the injection needle 14 is plunged into the body, and the preparatory operation (needle insertion operation) prior to pharmaceutical injection is complete.

Next, in S22, when the preparatory operation (needle insertion operation) prior to pharmaceutical injection is complete, the operation of pharmaceutical injection is commenced.

In the pharmaceutical injection operation, the push-in rate of the separation gasket 18 by the piston drive motor 10 is switched to the push-in rate V4 so as to be higher than the push-in rate V3 (V4>V3).

Since it is unlikely that there will be leakage from the distal end of the injection needle 14 during the pharmaceutical injection operation, the speed at which the piston 5 is moved can be increased.

Then, in S23, the piston drive motor 10 continues to move at the push-in rate V4 until the distal end position of the separation gasket 18 reaches the position LA.

Figure 9F:
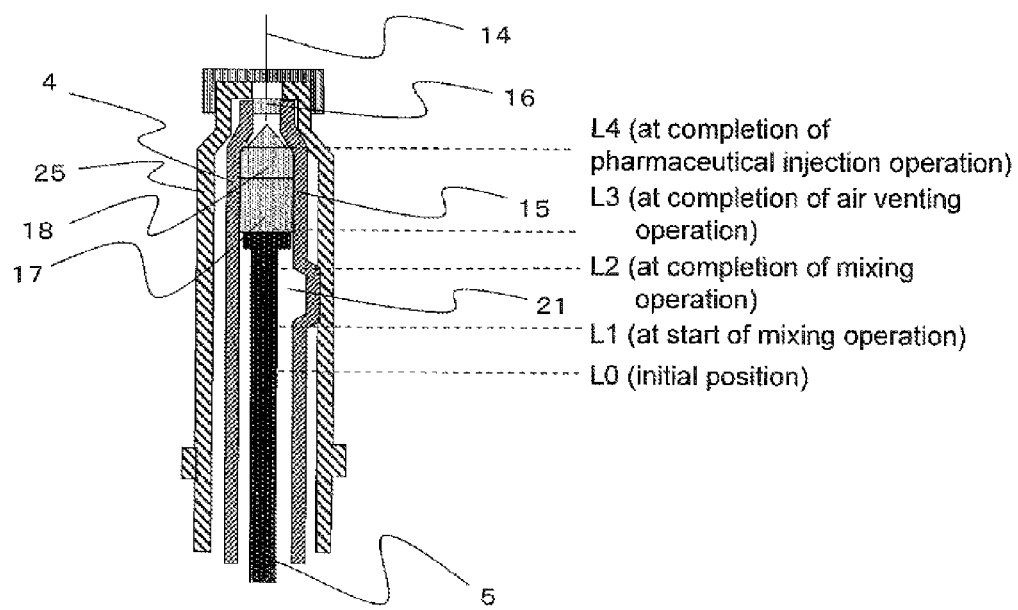
FIG. 9F is a cross section of the operating state during mixing in the pharmaceutical injection device in FIG. 1.

As shown in FIG. 9F, the movement distance from the position L3 to the position L4 indicates the movement distance up to where the separation gasket 18 reaches the inclined portion of the distal end of the pharmaceutical syringe 4. Position information about this movement distance L4 is stored ahead of time in the memory 46.

Finally, in S24, the needle retraction operation is commenced when the distal end position of the separation gasket 18 reaches the position L4. In the needle retraction operation, the piston drive motor 10 is halted and the needle insertion and retraction drive motor 12 is driven.

This needle retraction operation involves driving the needle insertion and retraction drive motor 12 to move the pharmaceutical syringe mounting portion 3 to the rear end side, and thereby stowing the injection needle 14 inside the injection needle insertion and retraction opening 1.

After this, in S25, when the pharmaceutical syringe mounting portion 3 reaches its initial position prior to the needle insertion operation, the needle retraction operation is complete and the operation of pharmaceutical injection into the body is ended.

FIG. 8 is a graph of the operating state during mixing with this pharmaceutical injection device. The vertical axis is the applied voltage (value) to a motor driver (not shown) for driving the piston drive motor 10, and the horizontal axis is the rear end position or distal end position of the separation gasket 18, showing a simulation of the flow of the operation at the above-mentioned push-in rates (V1, V2, V3, and V4).

Although not discussed detail here, the push-in rates are determined by changing the voltage values of a piston speed control signal (such as 1.0 volt for V1 and V4, 0.8 volt for V2, and 0.7 volt for V3). It can be seen that as the piston 5 is moved, the push-in rate V2 when the liquid pharmaceutical 20 passes through the bypass 21 is lower than the initial push-in rate V1, the push-in rate V3 during air venting is lower than the push-in rate V2, and the push-in rate V4 during pharmaceutical injection is higher than the push-in rate V3.

The graph in FIG. 8 is just one example, and a waiting period for user manipulation selection can be allocated as needed, such as between V2 and V3, or between V3 and V4. In this case, the mixing operation can be temporarily halted so that the various speeds are all zero. This is generally how the settings are made.

In the above description, position information about L0, L1, L2, L3, and L3 indicated where the distal end position or rear end position of the separation gasket 18 was located within the pharmaceutical syringe 4, but the above-mentioned control may be accomplished with the movement distance of the piston 5 at a separate stage.

As discussed above, the pharmaceutical injection device in this embodiment is such that in the pharmaceutical mixing operation, the push-in rate V2 at the point when the separation gasket 18 passes through the bypass 21 is set lower than the push-in rate V1 when the separation gasket 18 is pushed in until it comes into contact with the bypass 21. Consequently, the liquid pharmaceutical 20 flows gently through the bypass 21 to the solid pharmaceutical 19 side. As a result, leakage from the distal end gasket 16 side can be reduced during this pharmaceutical mixing operation, the surroundings can be kept clean, without the pharmaceutical splashing onto the surrounding area when the pharmaceutical injection device is operated by the user, and the automatic mixing of the pharmaceuticals can be carried out easily and safely.

The basic configuration and operation in this embodiment will be understood from the above description, and the most salient feature of this embodiment will now be described.

In this embodiment, a pharmaceutical formed by dissolving the solid pharmaceutical 19 in the liquid pharmaceutical 20 as shown in FIG. 9E was injected all at once as shown in FIG. 9F. However, the pharmaceutical thus obtained will sometimes be divided up into injections of a specific amount given over a plurality of days. In this case, the pharmaceutical syringe 4 that still contains some pharmaceutical is removed from the pharmaceutical syringe mounting portion 3 and stored in a refrigerator, for example. The main feature of this embodiment is that a warning display is given in regard to this storage.

This warning display in regard to storage will now be described in detail.

Figure 10:
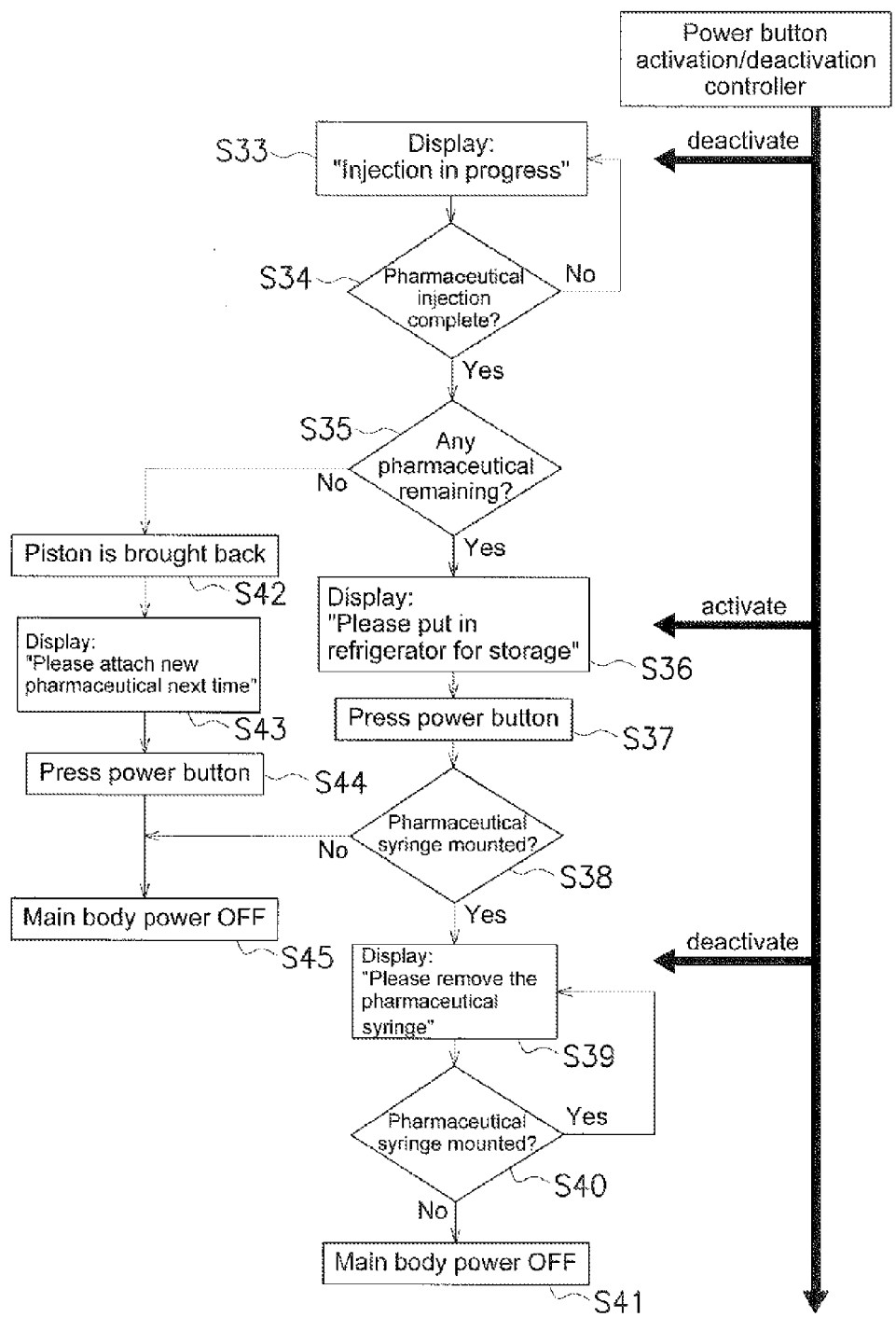
FIG. 10 is a flowchart of the operational control of the pharmaceutical injection device in FIG. 1.

FIG. 10 shows the flow of control when the pharmaceutical inside the pharmaceutical syringe 4 is injected in a specific amount over a plurality of days, as discussed above. A program for performing the control shown in FIG. 10 is stored in the ROM 38.

In S33, a display of "Injection in progress" is given on the display section 35 at the time of the first injection.

In S34, it is determined whether or not the injection of the pharmaceutical is complete. This is determined from the amount of movement of the piston 5, which has been set ahead of time. More specifically, the injection amount for each time is stored in the memory 46, and is determined by the amount of movement of the piston 5. The amount of movement of the piston 5 is sensed by the encoder 26.

In S35, the amount of pharmaceutical remaining in the pharmaceutical syringe 4 is sensed. Whether or not there is any pharmaceutical remaining in the pharmaceutical syringe 4 can also be determined from the amount of movement of the piston 5.

If it is determined that some pharmaceutical is remaining, a display of "Please put in refrigerator for storage" is given on the display section 35. In this state, in S37, for example, the power will not come to off even if the power button 31 is pressed, and then in S38 a pharmaceutical mounting determination is performed.

If it is determined by this remaining pharmaceutical determination that some pharmaceutical still remains, in S39 a warning message of "Please remove the pharmaceutical syringe" is given on the display section 35.

In S38, it is determined by the syringe cover detector switch 30 whether or not the pharmaceutical syringe 4 has been removed. Specifically, the pharmaceutical syringe 4 containing the pharmaceutical is housed in the syringe cover 25 as mentioned above. Accordingly, in removing the pharmaceutical syringe 4 from the pharmaceutical syringe mounting portion 3, the syringe cover 25 must also be removed. In view of this, the syringe cover detector switch 30 detects whether or not the syringe cover 25 has been mounted. As a result, it is detected that the pharmaceutical syringe 4 has been removed. The distal end cap 23 must always be removed before removing the syringe cover 25.

Next, in S39, the above-mentioned warning display of "Please remove the pharmaceutical syringe" is given on the display section 35. After this, pharmaceutical mounting determination is again performed in S40. Here again, the warning display is checked, and if the pharmaceutical syringe 4 has been removed along with the syringe cover 25 from the pharmaceutical syringe mounting portion 3 as discussed above, the power goes off in S41. At this point, the piston 5 is held in its position, and when the push-in gasket 17 is driven by a specific amount from that position upon the next pharmaceutical injection, a specific amount of pharmaceutical can again be injected.

That is, when one pharmaceutical injection is over, the pharmaceutical syringe 4 is removed from the pharmaceutical syringe mounting portion 3 and stored in a refrigerator. Accordingly, at the next pharmaceutical injection, the stored pharmaceutical syringe 4 must again be mounted to the syringe cover 25, and then mounted to the pharmaceutical syringe mounting portion 3. The piston 5 at this point is held in the position it had at the end of the last injection, so in this state the piston 5 and the push-in gasket 17 are in contact. The piston 5 then moves from this position by a specific amount to the left in FIG. 2 in order to inject the amount stored in the memory 46.

Again at the next pharmaceutical injection, since the distal end cap 23 is mounted, syringe cover detection is performed, and pharmaceutical injection is carried out smoothly.

In S35, in a state in which all of the pharmaceutical in the pharmaceutical syringe 4 has been injected (see FIG. 9F), the end of pharmaceutical injection is detected by the encoder 26.

Thus, in S42, the piston is brought back to the right in FIG. 2.

Next, in S43, a display of "Please attach new pharmaceutical next time" is given on the display section 35.

Next, in S44, when the power button 31 is pressed, even if the pharmaceutical syringe 4 has not be removed from the pharmaceutical syringe mounting portion 3, the power can be turned off in S45.

As discussed above, in this embodiment the encoder 26 is used to constitute a remaining pharmaceutical sensor. The amount of pharmaceutical remaining in the pharmaceutical syringe 4 can be sensed by this remaining pharmaceutical sensor (encoder 26). If it is confirmed that there is pharmaceutical in the pharmaceutical syringe 4 by the remaining pharmaceutical sensor (encoder 26), that is, that some pharmaceutical still remains, then a warning display is given on the display section 35 to recommend the removal of the pharmaceutical syringe 4 from the pharmaceutical syringe mounting portion 3.

Consequently, if there is some pharmaceutical remaining in the pharmaceutical syringe 4, the user can be prompted by a warning display on the display section 35 to remove the pharmaceutical syringe 4 from the pharmaceutical syringe mounting portion 3 and, for example, store it in a refrigerator. As a result, the management of the pharmaceutical syringe 4 can be performed properly.

INDUSTRIAL APPLICABILITY

With the pharmaceutical injection device of the present invention, if there is some pharmaceutical remaining in the pharmaceutical syringe, a warning display on the display section prompts the user to remove the pharmaceutical syringe from the pharmaceutical syringe mounting portion and store it in a refrigerator, and as a result, the management of the pharmaceutical syringe can be performed properly. Therefore, this device is expected to find wide application in the field of pharmaceutical injection devices and so forth in which a pharmaceutical mixing operation is required.

REFERENCE SIGNS LIST 1 injection needle insertion and retraction opening
2 main body case 3 pharmaceutical syringe mounting portion
4 pharmaceutical syringe
5 piston
6 drive mechanism
7 controller
7a substrate
8 orientation sensor
9 bolt
10 piston drive motor
11 female threads
12 needle insertion and retraction drive motor
13 bolt
14 injection needle
15 cylinder
16 distal end gasket
17 push-in gasket
18 separation gasket
19 solid pharmaceutical
20 liquid pharmaceutical
21 bypass
22 housing
23 distal end cap
24 window
25 syringe cover
26 encoder (remaining pharmaceutical sensor)
27 control rod
28 distal end cap detector switch
29 control rod
30 syringe cover detector switch
31 power button
32 mix button
33 pharmaceutical injection button
34 end button
35 display section
36 rechargeable battery
37 central processing unit
38 ROM
39 orientation detecting section
39a orientation determination section
40 piston movement distance sensor
41 motor rotation controller
42 motor drive circuit
43 over-current detection circuit
44 buzzer
45 vibrator
46 memory

The invention claimed is:

1. A pharmaceutical injection device, comprising:
a main body case that has an opening through which an injection needle is inserted and retracted;
a pharmaceutical syringe mounting portion that is provided inside the main body case and to which a pharmaceutical syringe is removably mounted;
a piston that is provided movably with respect to the pharmaceutical syringe mounted to the pharmaceutical syringe mounting portion;
a drive mechanism configured to drive the piston, the drive mechanism including a piston drive motor configured to drive the piston;
a controller that is electrically connected to the drive mechanism;
a display section that is connected to the controller; and
a remaining pharmaceutical sensor that is connected to the controller and configured to sense the amount of pharmaceutical remaining in the pharmaceutical syringe from the amount of movement of the piston,
wherein, when the presence of a pharmaceutical is detected by the remaining pharmaceutical sensor, the controller causes the display section to display a warning that includes an express instruction that the pharmaceutical syringe be removed from the pharmaceutical syringe mounting portion and that the pharmaceutical syringe be stored in a refrigerator.

2. The pharmaceutical injection device according to claim 1,
wherein the controller turns off power of the device after the pharmaceutical syringe has been removed from the pharmaceutical syringe mounting portion following the display of a warning on the display section.

* * * * *